United States Patent [19]

Foulletier

[11] Patent Number: 4,748,285

[45] Date of Patent: May 31, 1988

[54] CATALYSTS AND PROCESS FOR GASEOUS PHASE FLUORINATION OF ALIPHATIC CHLORINATED DERIVATIVES

[75] Inventor: Louis Foulletier, Oullins, France

[73] Assignee: Produits Chimiques Ugine Kuhlmann, Courbevoie, France

[21] Appl. No.: 935,144

[22] Filed: Nov. 25, 1986

Related U.S. Application Data

[60] Continuation of Ser. No. 429,080, Sep. 30, 1982, abandoned, which is a division of Ser. No. 324,437, Nov. 24, 1981, Pat. No. 4,439,534.

[30] Foreign Application Priority Data

Dec. 29, 1980 [FR] France .................................. 80 27659

[51] Int. Cl.$^4$ ........................ C07C 17/20; C07C 45/00
[52] U.S. Cl. ..................................... 570/169; 568/407
[58] Field of Search ................. 570/165, 169, 170, 175

[56] References Cited

U.S. PATENT DOCUMENTS

| | | | |
|---|---|---|---|
| 2,819,229 | 1/1958 | Strecker et al. | 252/448 |
| 3,157,707 | 11/1964 | Clark et al. | 252/467 X |
| 3,258,500 | 6/1966 | Swamer et al. | 570/169 |
| 3,426,009 | 2/1969 | Chapman et al. | 260/653.7 |
| 3,591,646 | 7/1971 | Vecchio et al. | 570/165 |
| 3,681,259 | 8/1972 | Vesely | 252/448 |
| 3,755,477 | 8/1973 | Firth et al. | 570/165 |
| 3,978,145 | 8/1976 | Knaak | 570/165 |
| 4,218,430 | 8/1980 | Biggerstaff | 252/448 |

*Primary Examiner*—J. E. Evans
*Attorney, Agent, or Firm*—Pennie & Edmonds

[57] ABSTRACT

This invention relates to catalysts for gaseous phase fluorination of aliphatic chlorinated derivatives by hydrofluoric acid. The catalysts comprise chromium oxide microspheres obtained by a sol-gel process. This invention also relates to gaseous phase fluorination processes for aliphatic chlorinated derivatives utilizing these catalysts.

24 Claims, No Drawings

CATALYSTS AND PROCESS FOR GASEOUS PHASE FLUORINATION OF ALIPHATIC CHLORINATED DERIVATIVES

This is a continuation of application Ser. No. 429,080, filed Sept. 30, 1982, now abandoned, which was a division of application Ser. No. 324,437, filed Nov. 24, 1981 now U.S. Pat. No. 4,439,534.

TECHNICAL FIELD

This invention relates to catalysts for gaseous phase fluorination of aliphatic chlorinated derivatives by hydrofluoric acid. The catalysts comprise chromium oxide microspheres obtained by a sol-gel process.

This invention also relates to gaseous phase fluroination processes of aliphatic chlorinated derivatives utilizing these catalysts.

BACKGROUND ART

Various catalysts have been proposed for fluorination processes which substitute fluorine atoms for chlorine. Frequently, these catalysts are oxides or halides of chromium, aluminum, cobalt, iron, titanium, nickel, copper, palladium or zirconium; which are unsupported or supported on active carbons or alumina.

The chromium catalysts are divided into three groups:
catalysts of chromium fluoride
catalysts of chromium oxyfluoride
catalysts of chromium oxide Chromium oxide catalysts are described, for example, in British Pat. No. 896,068 and U.S. Pat. No. 3,157,707. These catalysts are obtained by the dehydration of chromium hydroxide or by the reduction of chromium trioxide deposited on activated alumina.

French Pat. No. 1,369,782 discloses catalysts comprising non-supported chromium oxides obtained by the dehydration of chromium oxide.

U.S. Pat. No. 3,258,500 describes a catalyst having a anhydrous non-supported trivalent chromium base that is prepared by the reduction of chromium trioxide by ethanol and activated by heating in an inert atmosphere of 400°-600° C.

Other patents such as Japanese Applications Nos. 70.116696 and 74.131610, teach the reduction of chromium troixide by aldehydes or hydrazine.

Catalysts having a black chromium oxide base, obtained by the thermal decomposition of chromium trioxide, chromic hydroxide or chromic carbonate in the presence of air or oxygen, are disclosed in French Pat. No. 1,358,997.

U.S. Pat. No. 3,978,145 teaches that the chromium oxide catalysts previously prepared are not amorphous, but have the crystalline structure of an orthorhombic γ—CrOOH. The disclosure proposes catalysts having improved utility, comprising an hexagonal form of this hydroxide-oxide of chromium.

All of the chromium oxide catalysts of the prior art are more or less suitable for gaseous phase fluorination of aliphatic chlorinated derivatives in fixed bed reactor systems. In fluidized bed reactors, which require particles of regular form and homogeneous granulometry, the prior art catalysts are poorly adapted to fluorination processes. Simple grinding of the catalysts, followed by sifting for the selection of suitable-sized particles provides particles of irregular form and leads to a significant loss of the catalyst.

A further disadvantage of known chromium oxide catalysts is a weak resistance to crystallization that ultimately contributes to a shortening of their effective life span. Most of these catalysts yield a ratio relatively elevated in asymmetric isomers when they are used for the preparation of tetrachlorodifluoroethane, trichlorotrifluoroethane and dichlorotrifluoroethane. Ideally, the content of these asymmetric isomers should be as low as possible since they are more sensitive to hydrolysis and are, therefore, more corrosive.

SUMMARY OF THE INVENTION

This invention discloses gaseous phase fluorination catalysts for aliphatic chlorinated derivatives. The catalysts prepared according to this invention are amorphous chromium oxide catalysts, which are resistant to crystallization and are particularly adapted to fluidized bed reactors. The catalysts provide elevated levels of symmetric isomers of perchlorofluorinated derivatives of ethane comprising 2, 3 or 4 chlorine atoms.

These catalysts are in the form of microspheres of about 100 to 3,000 $\mu$m in diameter, preferably near 300 $\mu$m. The microspheres are prepared according to the sol-gel process which has been the subject of important studies on oxides of thorium, zirconium and uranium. The sol-gel process is described in an article by J. M. Fletcher, "Application of Sol-Gel Processes to Industrial Oxides", published in *Chemistry and Industry*, Jan. 13, 1968 at page 48. It is also known from the work of J. Duclaux "Hémicolloides Minéraux", published in *Bulletin de la Societe Chimique de France*, 1956 at page 1289, that hydroxides of chromium can be made in the form of sols.

The applicant has discovered that gaseous phase fluorination catalysts are frequently tainted by the formation of tar on their surfaces and that the use of gaseous phase fluorination catalysts in fluidized bed reactors is advantageous since they cause abrasion of the catalyst gains, thus eliminating any attached tar and promoting catalytic activity. The catalyst is uniquely consumed by attrition and there is no need to stop the reaction in order to reload the reactor with the catalyst.

DETAILED DESCRIPTION OF THE INVENTION

The process of preparing the chromium oxide microsphere catalysts of this invention comprises five steps:

(a) formation of a sol or a semi-colloidal suspension of hydroxide of chromium, (b) gelling of the sol, in the form of micropheres, at an elevated temperature in an organic solvent that is non-miscible or only partially miscible in water, (c) washing the microspheres with ammonia and water to eliminate the majority of anions, (d) drying the microspheres at a temperature of, advantageously, about 130° C., (e) thermally treating the microspheres at a temperature between about 200° and 500° C., in order to develop their catalytic activity.

The formation of a sol of chromium hydroxide may be effected by any known method, but preferably, the sol is formed from solutions of chromium salts such as chromium chloride or nitrate, that are partially neutralized by ammonia and that contain hexamethylenetetramine. This compound liberates a supplemental quantity of ammonia at the temperature of gelling of the sol and favors the formation of very spherical microspheres. Alternatively, the sol may be prepared by the reduction of an aqueous solution of chromium trioxide by an alcohol such as methanol.

The sol is then dispersed in a solvent that is non-miscible in water, such as a liquid hydrocarbon or a haloalkane or preferably, in a solvent that is partially miscible in water, such as an alcohol containing from between 4 and 8 carbon atoms. The preferred solvent is 2-ethylhexanol.

Various additives, such as wetting agents and thickening agents can be added to the sol and/or to the solvent in order to improve the sphericity of the microspheres. It is sometimes advantageous to add from 1 to 10% of colloidal silica to the sol, in order to improve the mechanical strength of the microspheres. The silica is eliminated by hydrofluoric acid in the course of the fluorination reactions. The silica also serves to increase the porosity of the catalyst.

In the case of solvents that are non-miscible in water, the gelling of the sol, which is dispersed into droplets, is effected by the evaporation of water. When the solvents are partially miscible in water, it is advantageous to use a gelling column, such as those described by P. Hass in the article "Preparation of Thoria and Mixed-Oxide Microspheres" published in *Industrial Engineering Chemistry, Product Research and Development*, 5, 236 (September 1966) and in Certificate of Addition No. 88,004 to French Pat. No. 1,418,499.

The sol of chromium hydroxide is injected at the top of the column by means of a tube of small diameter which is concentrically disposed to the interior of another tube of larger diameter through which a solvent that is partially miscible in water and that has been preheated to a temperature of 25°-140° C., arrives as a moving fluid. Both the diameter of the injector of the sol and the flow of the moving fluid determine the diameter of the dispersed droplets and consequently, the final diameter of the microspheres.

The column itself is maintained at a temperature of 25° to 140° C. It is traversed, from bottom to top, by another fluid of warm solvent injected towards the bottom of the column, that escapes at the top by an overflow pipe after being enriched with water. This solvent is dehydrated by distillation-decantation and returns to the base of the column.

At the base of the column, the microspheres of the catalyst are collected in a receiver, which is preferably maintained at a temperature of 115° C. in order to avoid the formation of agglomerates.

The microspheres are then washed for several hours in concentrated ammonia, then in water. Subsequently, they are dried, advantageously, in air, at an temperature of about 130° C.

The microspheres thus obtained have practically no catalytic activity in fluorination reactions. Therefore, they must be subjected to a thermal treatment at approximately 400° C. for 1 to 72 hours, in an atmosphere of air or inert gas.

The chromium oxide microspheres have an amorphous structure and are particularly resistant to crystallization. A catalyst of this type utilized for close to 500 hours at 400° C., was still totally amorphous.

The catalysts of this invention demonstrate a certain selectivity in the fluorination of aliphatic chlorinated derivatives. They are particularly suitable for the fluorination of chlorinated and chlorofluorinated derivatives of methane and ethane and to the fluorination of hexachloroacetone. The catalysts are less suitable for the fluorination of chloronitriles.

EXAMPLES

The following examples demonstrate various methods of preparing the chromium oxide microspheres of this invention and their use in the catalysis of fluorination reactions in fluidized bed reactors. The examples are set forth for the purpose of illustration only and are not to be construed as limiting the scope of the invention in any manner.

Example 1: Preparation of Chromium Oxide Microspheres

A sol of chromium hydroxide is prepared by mixing chromium chloride, ammonia and hexamethylenetetramine, in an aqueous solution, in the following proportions:

| | |
|---|---|
| Chromium Chloride | 2 moles/l |
| Ammonia | 1.65 moles/l |
| Hexamethylenetetramine | 1.64 moles/l |

The apparatus used for gelling the sol comprises a glass column of 80 mm diameter and 1.50 m height, which is extended at its top by a zone of disengagement of 100 mm diameter. The sol is injected at the top of the disengagement zone at the rate of 0.40 l/h, through a tube having an interior diameter of 1 mm that is concentrically disposed to the interior of a tube of 3 mm interior diameter, through which 2-ethylhexanol is injected as a moving fluid at a temperature of 25° C. Towards the base of the column, another flow of 2-ethylhexanol, which has been preheated to a temperature of 120° C., is introduced at a rate of flow of 25 l/h. This flow of 2-ethylhexanol, which serves as a solvent for dehydration, runs through the column from bottom to top and exits by an overflow pipe located towards the top of the disengagement zone.

The chromium oxide microspheres are collected at the lower exterior of the column. The production of the apparatus is approximately 60 g/h.

The microspheres are copiously washed with concentrated ammonia then with water and are dried at 130° C. They are then activated at 400° C. for 5 hours in an atmosphere of air. The average diameter of the microspheres is approximately 300 μm.

The catalyst obtained shows the following characteristics:

| | |
|---|---|
| Density | 2,198 g/cm$^3$ |
| Specific Surface Area | 52.3 m$^2$/g |
| Specific Surface Area of Pores Having a Radius Greater Than or Equal to 250 Å | 0.05 m$^2$/g |
| Specific Surface Area of Pores Having a Radius of 50–250 Å | 0.765 m$^2$/g |
| Specific Surface Area of Pores Having a Radius of 40–50 Å | 1.61 m$^2$/g |

Example 2: Preparation of Chromium Oxide Microspheres

A sol is formed by continuously mixing 0.2 l/h of an aqueous solution containing 4 moles/l of chromium troxide (CrO$_3$) and 0.2 l/h of methanol. The reduction of the chromium trioxide is practically immediate, as is the color change.

The other conditions are identical to those of Example 1.

The production of the apparatus is 60 g/h of microspheres having a diameter of 284 μm.

Example 3: Preparation of Chromium Oxide Microspheres

An apparatus comprising a column of 300 mm diameter and 4.50 m height is injected, with the use of 18 needles of 1.5 mm interior diameter, with 20 l/h of a sol prepared from:

| | |
|---|---|
| Chromium Sulfate | 12 moles |
| Sesquioxide of Chromium (not calcined, in a fine powder) | 6 moles |
| Ammonia | 39.4 moles |
| Hexamethylenetetramine | 21.4 moles |
| Colloidal Silica LUDOX (registered trademark of the Du Pont de Nemours Co.) | 11.0 moles |

In this apparatus, no moving fluid is used to carry the microspheres.

The 2-ethylhexanol acting as the solvent of dehydration is supplied at the rate of 120 l/h. The temperature is maintained at 120° C.

The production is 4.32 kg/h of microspheres having a diameter of 0.8 to 2.0 mm.

Example 4: Fluorination of Hexachloroethane

This example demonstrates the use of the catalyst of Example 1 in the fluorination of hexachloroethane, formed in situ by the reaction of chlorine on tetrachloroethylene.

Through a fluidized bed reactor containing the catalyst and maintained at a temperature of 340° C., a mixture of hydrofluoric acid, chlorine and tetrachloroethylene, in a molar ratio of 4.26/1.1/1, is passed at the rate of 32 moles/h/l.

The rate of conversion of tetrachloroethylene is:
Tetrachlorodifluoroethane: 7%
Trichlorotrifluoroethane: 25%
Dichlorotetrafluoroethane: 57% (containing 83% symmetric isomer)
Monochloropentafluoroethane: 10%
The conversion rate of hydrofluoric acid is 83%.

If the same reaction is carried out under the same conditions at a temperature of 304° C., the rate of conversion of tetrachloroethylene is:
Tetrachlorodifluoroethane: 9%
Trichlorotrifluoroethane: 46%
Dichlorotetrafluoroethane,: (containing 92% symmetric isomer) 47%
Monochloropentafluoroethane: 3%

Example 5: Fluorination of Dichlorotetrafluoroethane

A mixture of dichlorotetrafluoroethane and hydrofluoric acid in a molar ratio of 2.42/1 and at a rate of flow of 8.6 moles/h/l is passed over the catalyst of Example 1 at 400° C., in the presence of a small amount of chlorine.

The rate of conversion of hydrofluoric acid is 52%
The rate of conversion of dichlorotetrafluoroethane is:
Monochloropentafluoroethane: 55%
Hexafluoroethane: 27%

Example 6: Fluorination of Dichlorodifluoromethane

A mixture of hydrofluoric acid and dichlorodifluoromethane, in a molar ratio of 2.9/1, and with a flow rate of 17.5 moles/h/l, is passed over the catalyst of Example 1 at a temperature of 400° C.

The rate of conversion of hydrofluoric acid is 67%.
The rate of conversion of dichlorodifluoromethane is:
Dichlorotrifluoromethane: 5%
Tetrafluoromethane: 95%

Example 7: Fluorination of Hexachloroacetone

The catalyst of Example 1 is used for the fluorination of hexachloroacetone under the following conditions:
Temperature: 300±50° C.
Molar Ratio HF/Cl$_3$C—CO—CCl$_3$: 7.7/1
Flow Rate: 4.8 moles/h/l A conversion rate of hydrofluoric acid of 76% is obtained.

The gas leaving the fluorination reactor contains, in moles, 75% hexafluoroacetone, 6% chloropentafluoroacetone and small quantities of dichlorotetrafluoroacetone and trichlorotrifluoroacetone.

I claim:

1. A gaseous phase fluorination process which comprises:
preparing catalysts having a chromium oxide base consisting essentially of unsupported amorphous chromium (II±) oxide having a diameter of between about 100 to 3,000 μm:
   (a) forming a sol or semi-colloidal suspension of hydroxide of chromium from a mixture comprising an aqueous solution of a chromium salt, ammonia, and hexamethylenetetramine;
   (b) gelling the sol in the form of microspheres, at an elevated temperature, in an organic solvent that is non-miscible or partially miscible in water;
   (c) washing the microspheres in ammonia and water;
   (d) drying the microspheres; and
   (e) thermally activating the microspheres at a temperature between about 200° and 500° C.; and
contacting chlorinated aliphatic hydrocarbons with hydrofluoric acid in the presence of said catalyst in a fluidized bed reactor for a sufficient time to produce fluorinated or fluorochlorinated aliphatic hydrocarbons.

2. The process according to claim 1 wherein the sol contains from 1 to 10% of colloidal silica in proportion to the dry materials.

3. The process according to claim 1 wherein the sol and/or the solvent contains wetting agents and/or thickening agents.

4. The process according to claim 1 wherein the gelling of the sol is effected in 2-ethylhexanol.

5. A gaseous phase fluorination process which comprises:
preparing catalysts having a chromium oxide base consisting essentially of unsupported amorphous chromium (III) oxide having a diameter of between about 100 to 3,000 μm, said chromium based catalysts prepared by:
   (a) forming a sol or semicolloidal suspension of hydroxide of chromium by the reduction of an aqueous solution of chromium trioxide by an alcohol;

(b) gelling the sol in the form of microspheres, at an elevated temperature, in an organic solvent that is non-miscible or partially miscible in water;
(c) washing the microspheres in ammonia and water;
(d) drying the microspheres; and
(e) thermally activating the microspheres at a temperature between about 200° and 500° C.; and
contacting chlorinated aliphatic hydrocarbons with hydrofluoric acid in the presence of said catalyst in a fluidized bed reactor for a sufficient time to produce fluorinated or fluorochlorinated aliphatic hydrocarbons.

6. The process according to claim 5 wherein the gelling of the sol is effected in 2-ethylhexanol.

7. A gaseous phase fluorination process which consists essentially of:
preparing catalysts having a chromium oxide base consisting essentially of unsupported amorphous chromium (III) oxide having a diameter of between about 100 to 3,000 μm by:
(a) forming a sol or semi-colloidal suspension of hydroxide of chromium from a mixture comprising an aqueous solution of a chromium salt, ammonia, and hexamethylenetetramine;
(b) gelling the sol in the form of microspheres, at an elevated temperature, in an organic solvent that is non-miscible or partially miscible in water;
(c) washing the microspheres in ammonia and water;
(d) drying the microspheres; and
(e) thermally activting the microspheres at a temperature between about 200° and 500° C.; and
contacting aliphatic chlorinated hydrocarbons with hydrofluoric acid in the presence of a catalyst in a fluidized bed reactor for a sufficient time to produce fluorinated or fluorochlorinated aliphatic hydrocarbons.

8. The process according to claim 7 wherein the sol contains from 1 to 10% of colloidal silica in proportion to the dry materials.

9. The process according to claim 7 wherein the sol and/or the solvent contains wetting agents and/or thickening agents.

10. The process according to claim 7 wherein the gelling of the sol is effected in 2-ethylhexanol.

11. A gaseous phase fluorination process which consists essentially of:
preparing catalysts having a chromium oxide base consisting essentially of unsupported amorphous chromium (III) oxide having a diameter of between about 100 to 3,000 μm by:
(a) forming a sol or semicolloidal suspension of hydroxide of chromium by the reduction of an aqueous solution of chromium trioxide by an alcohol;
(b) gelling the sol in the form of microspheres, at an elevated temperature, in an organic solvent that is non-miscible or partially miscible in water;
(c) washing the microspheres in ammonia and water;
(d) drying the microspheres; and
(e) thermally activating the microspheres at a temperature between about 200° and 500° C.; and
contacting aliphatic chlorinated hydrocabons with hydrofluoric acid in the presence of a catalyst in a fluidized bed reactor for a sufficient time to produce fluorinated or fluorochlorinated alipahtic hydrocarbons.

12. The process according to claim 11 wherein the gelling of the sol is effected in 2-ethylhexanol.

13. A gaseous phase fluorination process for forming symmetric isomers, of fluorinated aliphatic hydrocarbons which comprises:
preparing catalysts having a chromium oxide base consisting essentially of unsupported amorphous chromium (III) oxide having a diameter of between about 100 to 3,000 μm by:
(a) forming a sol or semi-colloidal suspension of hydroxide of chromium from a mixture comprising an aqueous solution of a chromium salt, ammonia, and hexamethylenetetramine;
(b) gelling the sol in the form of microspheres, at an elevated temperature, in an organic solvent that is non-miscible or partially miscible in water;
(c) washing the miscrospheres in ammonia and water;
(d) drying the microspheres; and
(e) thermally activating the microspheres at a temperature between about 200° and 500° C.; and
contacting chlorinated aliphatic hydrocarbons with hydrofluoric acid in the presence of said catalyst in a fluidized bed reactor.

14. The process according to claim 13 wherein the sol contains from 1 to 10% of colloidal silica in proportion to the dry materials.

15. The process according to claim 13 wherein the sol and/or the solvent contains wetting agents and/or thickening agents.

16. The process according to claim 13 wherein the gelling of the sol is effected in 2-ethylhexanol.

17. A gaseous phase fluorination process for forming symmetric isomers of fluorinated aliphatic hydrocarbons which comprises:
preparing catalysts having a chromium oxide base consisting essentially of unsupported amorphous chromium (III) oxide having a diameter of between about 100 to 3,000 μm, said chromium based catalysts prepared by:
(a) forming a sol or semicolloidal suspension of hydroxide of chromium by the reduction of an aqueous solution of chromium trioxide by an alcohol;
(b) gelling the sol in the form of microspheres, at an elevated temperature, in an organic solvent that is non-miscible or partially miscible in water;
(c) washing the microspheres in ammonia and water;
(d) drying the microspheres; and
(e) thermally activating the microspheres at a temperature between about 200° and 500° C.; and
contacting chlorinated aliphatic hydrocarbons with hydrofluoric acid in the presence of said catalyst in a fluidized bed reactor.

18. The process according to claim 17 wherein the gelling of the sol is effected in 2-ethylhexanol.

19. A gaseous phase fluorination process for forming symmetric isomers of fluorinated aliphatic hydrocarbons which consists essentially of:
preparing catalysts having a chromium oxide base consisting essentially of unsupported amorphous chromium (III) oxide having a diameter of between about 100 to 3,000 μm by:
(a) forming a sol or semi-colloidal suspension of hydroxide of chromium from a mixture comprising an aqueous solution of a chromium salt, ammonia, and hexamethylenetetramine;
(b) gelling the sol in the form of microspheres, at an elevated temperature, in an organic solvent that is non-miscible or partially miscible in water;
(c) washing the microspheres in ammonia and water;
(d) drying the microspheres; and (e) thermally activating the microspheres at a temperature between about 200° and 500° C.; and contacting chlorinated aliphatic hydrocarbons with hydrofluoric acid in the presence of said catalyst in a fluidized bed reactor.

20. The process according to claim 19 wherein the sol contains from 1 to 10% of colloidal silica in proportion to the dry materials.

21. The process according to claim 19 wherein the sol and/or the solvent contains wetting agents and/or thickening agents.

22. The process according to claim 19 wherein the gelling of the sol is effected in 2-ethylhexanol.

23. A gaseous phase fluorination process for forming symmetric isomers of fluorinated aliphatic hydrocarbons which consists essentially of:

preparing catalysts having a chromium oxide base consisting essentially of unsupported amorphous chromium (III) oxide having a diameter of between about 100 to 3,000 μm by:

(a) forming a sol or semicolloidal suspension of hydroxide of chromium by the reduction of an aqueous solution of chromium trioxide by an alcohol;

(b) gelling the sol in the form of microspheres, at an elevated temperature, in an organic solvent that is non-miscible or partially miscible in water;

(c) washing the microspheres in ammonia and water;

(d) drying the microspheres; and (e) thermally activating the microspheres at a temperature between about 200° and 500° C.; and contacting aliphatic chlorinated hydrocarbons with hydrofluoric acid in the presence of a catalyst in a fluidized bed reactor.

24. The process according to claim 23 wherein the gelling of the sol is effected in 2-ethylhexanol.

* * * * *

UNITED STATES PATENT AND TRADEMARK OFFICE
CERTIFICATE OF CORRECTION

PATENT NO. : 4,748,285

DATED : May 31, 1988

INVENTOR(S) : Louis Foulletier

It is certified that error appears in the above-identified patent and that said Letters Patent is hereby corrected as shown below:

In claim 1, line 5, delete "$(II^{\pm})$" and insert --(III)--

Signed and Sealed this

Twenty-fourth Day of January, 1989

*Attest:*

DONALD J. QUIGG

*Attesting Officer*  *Commissioner of Patents and Trademarks*